United States Patent [19]

Gorman et al.

[11] Patent Number: 5,288,479
[45] Date of Patent: Feb. 22, 1994

[54] EXTRUDABLE ELASTIC ORAL PHARMACEUTICAL GEL COMPOSITIONS AND METERED DOSE DISPENSERS CONTAINING THEM AND METHOD OF MAKING AND METHOD OF USE THEREOF

[75] Inventors: William G. Gorman, East Greenbush; Elio P. Mariani, Colonie, both of N.Y.

[73] Assignee: Sterling Drug, Inc., New York, N.Y.

[21] Appl. No.: 441,849

[22] Filed: Nov. 27, 1989

Related U.S. Application Data

[63] Continuation-in-part of Ser. No. 297,720, Jan. 17, 1989, abandoned.

[51] Int. Cl.$^5$ .............................. A61K 7/16
[52] U.S. Cl. ........................ 424/49; 424/401
[58] Field of Search ............... 424/49, 78; 514/629

[56] References Cited

U.S. PATENT DOCUMENTS

| | | |
|---|---|---|
| 4,511,068 | 4/1985 | Bossina . |
| 4,565,692 | 1/1986 | Mulvey et al. ............... 424/49 |
| 4,569,838 | 2/1986 | deVries ......................... 424/49 |
| 4,639,367 | 1/1987 | Mackles . |
| 4,685,594 | 8/1987 | Czech . |
| 4,702,905 | 10/1987 | Mitchell et al. ............... 424/57 |
| 4,708,834 | 11/1987 | Cohen et al. . |

FOREIGN PATENT DOCUMENTS 8503439  8/1985  PCT Int'l Appl. .

OTHER PUBLICATIONS

Physicians' Desk Reference for Nonprescription Drugs, 9th Edition, 1988, title page and pp. 423 and 667.
The Merck Index, Tenth Edition, 1983, Monographs 169, 228, 229, 1848 and 4177.
Calmar Inc. Brochure entitled "Product Dispenser News the High Viscosity Dispenser" (six pages).

Primary Examiner—Thurman K. Page
Assistant Examiner—Peter F. Kulkosky
Attorney, Agent, or Firm—Theodore C. Miller; Paul E. Dupont

[57] ABSTRACT

Extrudable elastic oral pharmaceutical gel compositions, especially containing acetaminophen as the therapeutically active agent, and manually operable metered dose dispensers containing them and method of making and method of use thereof are disclosed.

4 Claims, No Drawings

EXTRUDABLE ELASTIC ORAL PHARMACEUTICAL GEL COMPOSITIONS AND METERED DOSE DISPENSERS CONTAINING THEM AND METHOD OF MAKING AND METHOD OF USE THEREOF

CROSS REFERENCE TO RELATED APPLICATION

This application is a continuation-in-part of our copending application Ser. No. 07/297,720 filed Jan. 17, 1989, now abandoned.

BACKGROUND OF THE INVENTION

1. Field of the Invention

The invention relates to extrudable elastic oral pharmaceutical gel compositions and metered dose dispensers containing them and method of making and method of use thereof.

2. Information Disclosure Statement

Cohen et al. U.S. Pat. No. 4,708,834 issued Nov. 24, 1987 describes pharmaceutical gel compositions as fills for gelatin capsules. The fill compositions are described as "comprising an aqueous solution or dispersion of a polysaccharide gum and a pharmaceutically-active compound". Most of the water thereof is described as being removed after encapsulation by drying the capsules. Acetaminophen and niacin fill compositions and capsules are specifically described.

There is a need for oral pharmaceutical compositions for pediatric and adult/geriatric use in an easy to use metered dose form. An attempt to fill this need is shown by Mackles U.S. Pat. No. 4,639,367 issued Jan. 27, 1987, which describes "stable, edible anhydrous aerosol foam[s] or whip[s] capable of suspending up to 50% by weight of a dispersed solid . . . prepared from a foamable, edible anhydrous liquid oil; a foaming agent; and controlled amounts of a food grade propellant which are sufficient to produce a stable foam rather than a spray." Such products appear to be illustrated by Extra Strength MAALOX® WHIP ™ Antacid brand of magnesium and aluminum hydroxides oral suspension, which is described by Physicians' Desk Reference for Nonprescription Drugs (ninth edition, 1988, pp. 423 and 667). These compositions suffer the disadvantages of high caloric content due to the edible oil, potential for gastric and intestinal distress due to the aerosol propellant, inexact metering and tendency for the aerosol dispenser nozzle to clog due to the particulate nature of the compositions. The presently described and claimed invention overcomes all of these disadvantages.

SUMMARY OF THE INVENTION

In a composition of matter aspect the invention is an extrudable elastic oral pharmaceutical gel composition being a solution and consisting essentially of by weight/volume from about 0.1% to about 50% of a therapeutically active agent or a mixture of two or more therapeutically active agents, from about 5% to about 40% of an alcoholic solvent selected from the group consisting of ethanol, propylene glycol, glycerin and polyethylene glycol having the structural formula $H-(OCH_2CH_2)_n-OH$ wherein n is an integer from 4 to 180 or a mixture thereof, from about 5% to about 40% of a hexitol selected from the group consisting of sorbitol, mannitol and hydrogenated maltose syrup or a mixture thereof, from about 25% to about 85% of water, and from about 0.2% to about 5% of a seaweed polysaccharide selected from the group consisting of agar, algin, carrageenan and furcelleran or a mixture thereof.

In a combined manufacture and composition of matter aspect the invention is an above-described extrudable elastic oral pharmaceutical gel composition contained within a manually operable dispenser capable of delivering a metered dose of the composition as an extrudate.

In a first process aspect the invention is the method of making the combined manufacture and composition of matter aspect of the invention which comprises first preparing an above-described extrudable elastic oral pharmaceutical gel composition by mixing the incredients thereof and then filling an above-described manually operable dispenser therewith.

In a second process aspect the invention is the method of using the combined manufacture and composition of matter aspect of the invention which comprises dispensing a metered dose of an above-described extrudable elastic oral pharmaceutical gel composition from an above-described manually operable dispenser.

DETAILED DESCRIPTION OF THE INVENTION INCLUSIVE OF THE PREFERRED EMBODIMENTS

The therapeutically active agent can be any medicinal compound which is soluble in the composition, stable on admixture with the other ingredients of the composition and effective on oral administration of the composition or a combination of any two or more such compounds and is preferably selected from the group consisting of analgesics, antihistamines, antitussives, expectorants and oral nasal decongestants. The analgesic is preferably selected from the group consisting of acetaminophen and ibuprofen. The antihistamine is preferably selected from the group consisting of brompheniramine maleate, chlorpheniramine maleate, doxylamine succinate, phenidamine tartrate and pyrilamine maleate. The antitussive is preferably selected from the group consisting of codeine or a pharmaceutically acceptable acid addition salt thereof, dextromethorphan or a pharmaceutically acceptable acid addition salt thereof and diphenhydramine hydrochloride. The expectorant is preferably selected from the group consisting of guaifenesin and potassium guaicacolsulfonate. The oral nasal decongestant is preferably selected from the group consisting of phenylephrine or a pharmaceutically acceptable acid addition salt thereof, phenylpropanolamine or a pharmaceutically acceptable acid addition salt thereof and pseudoephedrine or a pharmaceutically acceptable acid addition salt thereof.

The polyethylene glycols having the structural formula $H-(OCH_2CH_2)_n-OH$ wherein n is an integer from 4 to 180 have molecular weights in the range from 194 to 7948, respectively, and can also be defined thereby, that is, as having molecular weights in the range from about 200 to about 8000. A mixture of two or more such polyethylene glycols can also be used. The names thereof used herein are the CTFA (The Cosmetic, Toiletry and Fragrance Association, Inc., 1110 Vermont Avenue, N.W., Washington, D.C. 20005) Adopted Names as defined in the CTFA Cosmetic Ingredient Dictionary (Third Edition, 1982) and supplements thereof. The names given therein for the polyethylene glycols all begin with a acronym PEG and range from PEG-4 (the first entry) to PEG-90M (the last entry). PEG-4 defines the polyethylene glycol of the foregoing structural formula wherein "n has an average value of 4". Since the polyethylene glycols are synthetic polymers, the value of n is not the same for every molecule of a sample and is therefore expressed as an average. In PEG-90M "n has an average value of 90000". PEG-6-32 is defined as a mixture of PEG-6 wherein n has an average value of 6 and PEG-32 wherein n has an average value of 32. Accordingly the CTFA Adopted Names of the polyethylene glycols reflect the molecular structures thereof.

Hydrogenated maltose syrup is defined as the substance made by hydrogenation of special high maltose syrup obtained from enzymatic hydrolsis of food starch. The substance contains a significant amount of sorbitol. LYCASIN ® brand of hydrogenated maltose syrup is sold by Roquette Corporation.

The seaweed polysaccharides are described generally and specifically in a book entiled "Industrial Gums" (subtitle, "Polysaccharides and Their Derivatives", Second Edition; Roy L. Whistler, editor; James N. BeMiller, assistant editor; Academic Press, New York and London, 1973), wherein they are also referred to as seaweed extracts (heading of chapters III-IX) and seaweed gums (chapter I by Roy L. Whistler, page 8). A separate chapter among chapters III-IX is devoted to each of agar (chapter III by H. H. Selby and W. H. Wynne), algin (chapter IV by William H. McNeely and David J. Pettitt), carageenan (chapter V by Gordon A. Towle) and furcelleran (chapter VII by E. Bjerre-Petersen, J. Christensen and P. Hemmingsen). Each of these substances is also described by a monograph of the Merck Index (Tenth Edition, 1983): agar by monograph 169, algin by monograph 228 (monograph 229 describes alginic acid), carageenan by monograph 1848 and furcelleran by monograph 4177.

The concentration of therapeutically active agent in the composition is determined by the effective dose of the therapeutically active agent, the amount of composition to be delivered in a single dose and the number of doses to be administered in a given period of time. A typical single dose of composition is about 2.5 ml. If for example the effective dose of therapeutically active agent is 100 mg. and the dose is 2.5 ml., the concentration of therapeutically active agent is 4% by weight/volume. Table I shows the range of effective daily doses of each of the above-named preferred therapeutically active agents whereby the concentration thereof, depending on the number of doses to be administered per day, is determined.

TABLE I

Effective Daily Doses of Therapeutically Active Agents

| Therapeutically Active Agent | Range of Effective Daily Dose (mg.) |
|---|---|
| Acetaminophen | 800-4000 |
| Ibuprofen | 200-1200 |
| Brompheniramine Maleate | 6-24 |
| Chlorpheniramine Maleate | 6-24 |
| Doxylamine Succinate | 18.75-75 |
| Phenindamine Tartrate | 37.5-150 |
| Pyrilamine Maleate | 50-200 |
| Codeine | 30-120 |
| Dextromethorphan | 30-120 |
| Diphenhydramine Hydrochloride | 37.5-150 |
| Guaifenesin | 600-2400 |
| Potassium Guaiacolsulfonate | 75-300 |
| Phenylephrine | 15-60 |
| Phenylpropanolamine | 37.5-150 |
| Pseudoephridine | 60-240 |

In addition to the essential ingredients the composition can contain one or more pharmaceutical adjuncts, which can include preservatives, dyes and flavors.

The compositions of the invention are generally prepared by gently mixing the ingredients at a temperature in the range of 0°-100° C., preferably 20°-70° C. When the solubility of the therapeutically active agent in water is low, it is first dissolved in the alcoholic solvent or solvent mixture. So as not to precipitate it the water is added slowly and carefully. The seaweed polysaccharide can be added at any stage of the mixing but is preferably added last to avoid gelling during the mixing. Vigorous mixing is avoided to minimize entrapment of air bubbles in the composition upon gelling. The following composition of the invention containg acetaminophen as the therapeutically active agent was prepared.

EXAMPLE

| Ingredient | % Weight/Volume |
|---|---|
| Acetaminophen, USP | 3.20x |
| PEG-6-32 | 20.0xx |
| Propylene Glycol | 5.00x |
| Glycerin | 5.00x |
| Sorbitol Solution, 70% | 40.0xx |
| Potassium Sorbate | 0.300 |
| Benzoic Acid | 0.100 |
| FD & C Red # 40 Dye | 0.010 |
| Cherry/Raspberry Flavor | 0.094 |
| Calcium Saccharin | 0.180 |
| Carrageenan | 1.50x |
| Purified Water to make | 100.0xx |

In this composition the potassium sorbate and benzoic acid are preservatives. The PEG-6-32, propylene glycol, glycerin, sorbitol solution and about 90% of the purified water were placed into a manufacturing kettle and warmed to about 45° C. with gentle mixing. The acetaminophen, potassium sorbate, benzoic acid and calcium saccharin were added with further mixing. The mixture was cooled to room temperature and the dye and flavor were added with further mixing. The remainder of the purified water was added with further mixing. The prefered pH is 4.5 and can be adjusted at this stage if necessary with hydrochloric acid or sodium hydroxide. The mixture was warmed to 65° C. and the carrageenan was added with further mixing until dissolved. The resulting mixture, which was a solution, was poured into a manually operable dispenser capable of delivering a metered dose of the composition as an extrudate and allowed to cool. The dispenser dispensed a metered dose of about 2 ml. containing about 64 mg. of acetaminophen.

The compositions of the invention including that of the foregoing example are elastic, that is they coalesce if separated. They are not rigid or rubbery but are soft and can be extruded. They are formulated to be taken by mouth. A dose thereof can be measured out by weight or volume manually and administered directly, for example, by spoon from a jar, but the preferred means of administration is by metered dose from a manually operable dispenser similar to the type presently used for dispensing toothpastes and generally disclosed in U.S. Pat. Nos. 4,511,068 and 4,685,593. The metered dose can be dispensed into a spoon, then taken orally, thus avoiding manually measuring out the dose and thus providing a convenient dosage form for the very young, the very old and even those inbetween.

A preferred manually operable dispenser is sold by Calmar Inc. (40 Stirling Road, Watchung, N.J. 07060) under the name High Viscosity Dispenser (HVD) and is described by two brochures, one entitled Product Dispenser News and the other entitled FACT SHEET. The latter cites U.S. Pat. No. 4,511,608.

Another preferred manually operable dispenser is sold by The English Glass Company Limited (Scudamore Road, Leicester LE31UG, England) under the name VARIO Dispenser and is described by a brochure entitled THE NEW VARIO DISPENSER FROM englass ®.

A preferred combined manufacture and composition of matter aspect of the invention is the acetaminophen gel composition of the foregoing example contained within the HVD or VARIO Dispenser.

A preferred first process aspect of the invention is the method of making the preferred combined manufacture and composition of matter aspect of the invention which comprises first preparing the acetaminophen gel composition of the foregoing example by mixing the ingredients thereof and then filling the HVD or VARIO Dispenser therewith.

A preferred second process aspect of the invention is the method of using the preferred combined manufacture and composition of matter aspect of the invention which comprises dispensing a metered dose of the acetaminophen gel composition of the foregoing example from the HVD or VARIO Dispenser.

We claim:

1. An extrudable elastic oral pharmaceutical gel composition being a solution and consisting essentially of by weight/volume from about 0.1% to about 50% of acetaminophen, from about 5% to about 40% of a mixture of propylene glycol, glycerin and polyethylene glycol having the structural formula $H-(OCH_2CH_2)_n-OH$ wherein the polyethylene glycol is a mixture of the polyethylene glycol wherein n is 6 and the polyethylene glycol wherein n is 32, from about 5% to about 40% of a hexitol selected from the group consisting of sorbitol, mannitol and hydrogenated maltose syrup or a mixture thereof, from about 25% to about 85% of water, and from about 0.2% to about 5% of a seaweed polysaccharide selected from the group consisting of agar, algin, carrageenan and furcelleran or a mixture thereof.

2. A composition according to claim 1 wherein the hexitol is sorbitol.

3. A composition according to claim 2 wherein the seaweed polysaccharide is carrageenan.

4. A composition according to claim 3 consisting essentially of by weight/volume about 3.2% acetaminophen, about 5% propylene glycol, about 5% glycerin, about 28% sorbitol, about 20% of the polyethylene glycol mixture, about 1.5% carrageenan and about 36.6% water.

* * * * *